(12) United States Patent
West et al.

(10) Patent No.: US 6,576,729 B2
(45) Date of Patent: Jun. 10, 2003

(54) SILYLENE CATALYSIS OF OLEFIN POLYMERIZATION

(75) Inventors: Robert C. West, Madison, WI (US); Daniel F. Moser, Middleton, WI (US); Michael P. Haaf, Lititz, PA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/965,167

(22) Filed: Sep. 27, 2001

(65) Prior Publication Data

US 2002/0042489 A1 Apr. 11, 2002

Related U.S. Application Data

(60) Provisional application No. 60/238,172, filed on Oct. 5, 2000.

(51) Int. Cl.[7] .............................. C08F 2/00; C08F 4/00
(52) U.S. Cl. .................. 526/194; 526/348; 556/406; 556/407; 556/413
(58) Field of Search ................... 526/194, 348; 556/406, 407, 413

(56) References Cited

U.S. PATENT DOCUMENTS 5,728,856 A   3/1998   Denk

FOREIGN PATENT DOCUMENTS

| DE | 4316883 A1 | 11/1994 |
|---|---|---|
| EP | 0 611 772 A2 * | 8/1994 |

OTHER PUBLICATIONS

Denk, http://www.chem.utoronto.ca/staff/denk–m.himl.*

Joachim Heinicke et al., Unsymmetrical Carbene homologues: Isolable . . . , 4 J. Chem. Eur. 541–545 (1998).

M. Haaf et al., Synthesis and Reactivity of a Stable Silylene, 120 J. Am. Chem. Soc. 12714–12719 (1998).

J. Lehmann et. al., Core Excitation Spectroscopy of Stable Cyclic Diaminocarbenes, –silylenes, and –germylenes, 18 Organo. 1862–1872 (1999).

Sep. 20, 2000 printout by Michael Denk. While Sep. 20, 2000 content would not be prior to applicants' invention, applicants note that the end of the excerpt claims that the page was last updated on Feb. 5, 1996.

M. Denk et al., Synthesis and Structure of a Stable Silylene, 116 J. Am. Chem. Soc. 2691–2692 (1994).

* cited by examiner

*Primary Examiner*—David W. Wu
*Assistant Examiner*—Ling-Siu Choi
(74) *Attorney, Agent, or Firm*—Quarles & Brady LLP

(57) ABSTRACT

Disclosed herein are methods for producing a polymer. One polymerizes monomers selected from alkene monomers and terminal alkyne monomers, in the presence of a catalyst which is a silylene. The catalyst can be a heterocyclic amido silylene which is at least partially unsaturated within the ring. Also disclosed are polymers produced by the above methods, and improved methods for producing the catalysts.

3 Claims, No Drawings

SILYLENE CATALYSIS OF OLEFIN POLYMERIZATION

CROSS-REFERENCE TO RELATED APPLICATION

This is a continuation of provisional U.S. application 60/238,172, filed Oct. 5, 2000, to which priority is hereby claimed.

STATEMENT REGARDING FEDERALLY SPONSORED RESEARCH

This invention was made with United States government support awarded by the following agency: NSF 9901266. The United States has certain rights in this invention.

BACKGROUND OF INVENTION

The present invention relates to divalent silicon compounds which are known as silylenes. More particularly, it relates to the use of these compounds to catalyze olefin polymerization reactions.

In recent years there have been efforts directed towards the isolation of compounds containing divalent silicon centers, particularly heterocyclic amido variants. See M. Haaf et al., 120 J. Am. Chem. Soc. 12714–12719 (1998) (synthesis of silylenes); J. Lehmann et al., 18 Organomet. 1862–1872 (1999) (study of silylenes); and U.S. Pat. No. 5,728,856 (synthesis of silylenes). The disclosures of these publications, and of all other publications referred to herein, are incorporated by reference as if fully set forth herein.

While several syntheses of these compounds have been proposed, these syntheses were often inefficient. A need still exists for ways to improve their efficiency, particularly with respect to the synthesis of heterocyclic silylenes.

In any event, these compounds were originally developed in order to provide a new class of reactive components that could be combined with other materials in varied synthesis reactions. It is now desired to find still other uses for them.

Synthesis of olefin polymers from monomers typically requires the use of a catalyst to assist in the polymerization reaction. These catalysts are often inefficient, complex, and expensive (e.g. a mixture of an organotitanium compound with an organoaluminum compound).

Other known techniques for polymerizing olefins involve a free radical process which typically results in highly branched polymers having soft properties. This can be a disadvantage when harder polymers are desired. Thus, a need still also exists for providing improved techniques for the production of olefin polymers.

BRIEF SUMMARY OF THE INVENTION

In one aspect the invention provides methods for producing a polymer. One polymerizes monomers selected from the group consisting of terminal alkene monomers and terminal alkyne monomers in the presence of a catalyst selected from the group consisting of silylenes.

The catalyst is preferably a cyclic (preferably heterocyclic) silylene, such as where the catalyst contains a [N—Si—N] moiety, with these three atoms being part of an at least partially unsaturated heterocyclic ring of at least five and no more than ten atoms.

In an especially preferred form, the catalyst is:

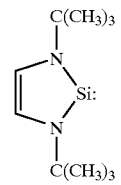

In another aspect the invention provides polymers produced by the above methods.

In yet another aspect, the invention provides an improved method for forming a compound having a structure selected from the group consisting of:

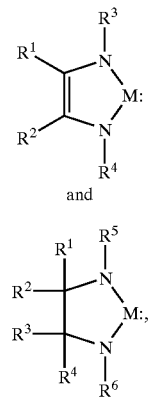

wherein M is Si and wherein $R^1$, $R^2$, $R^3$, and $R^4$, and if applicable $R^5$ and $R^6$, are individually selected from the group consisting of H and alkyl with less than 10 carbons. The method involves reacting a precursor ("Precursor") selected from the group consisting of:

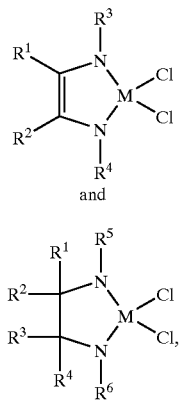

with elemental potassium. With respect to the Precursor, M is also Si, and $R^1$, $R^2$, $R^3$, and $R^4$, and if applicable $R^5$ and $R^6$, are also individually selected from the group consisting of H and alkyl with less than 10 carbons. The elemental potassium is added to the reaction at above 2.1 and less than 3.0 (preferably between 2.2 and 2.4) molar equivalents of the Precursor present in the reaction.

The preferred compound formed by this improved synthesis is:

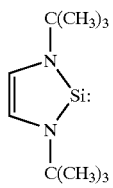

"Terminal alkene monomer" includes any polymerizable alkene monomers having a double bonded carbon at an end of the molecule, and mixtures thereof, including without limitation ethylene, propylene, 1-hexene, alkyl vinyl ethers such as ethyl vinyl ether, styrene, butadienes such as dimethyl butadiene, acrylonitrile, vinyl halides such as vinyl chloride, isobutene, and isoprene. As indicated by the inclusion of ethers, carbon and hydrogen need not be the only elements in the monomer.

"Terminal alkyne monomer" includes any polymerizable alkyne monomers with a triple bonded carbon at an end of the molecule, and mixtures thereof, including without limitation acetylene, phenyl acetylene, and other alkyl and aryl acetylenes. Again, carbon and hydrogen need not be the only elements in the monomer.

Preferred silylenes are compounds having a divalent silicon linked on each side to nitrogen such as: [(R$^1$R$^2$R$^3$C)R$^7$N]—Si—[NR$^8$(CR$^4$R$^5$R$^6$)], in which R$^1$, R$^2$, R$^3$, R$^4$, R$^5$, R$^6$, R$^7$ and R$^8$ are the same or different and each represents a hydrogen or halogen atom or an alkyl, aryl, alkoxy, aryloxy, amido or heteroaryl residue, and R$^7$ and R$^8$ can also represent the residue —CR$^1$R$^2$R$^3$ or —CR$^4$R$^5$R$^6$, and R$^7$ and R$^8$ can jointly form with the respective adjacent nitrogen atoms and the central silicon atom in an unsaturated heterocyclic ring with at least five ring atoms.

Where the catalyst has a heterocyclic ringed structure, it is preferred that any carbons other than those in the ring which includes the Si not exceed twenty carbons, and preferably not exceed six carbons. For example, the nitrogens can both be linked to tertiary butyl groups.

It has surprisingly been learned that silylenes can be efficient olefin polymerization catalysts, even at relatively low concentrations. Further, these compounds hold out the possibility of creating variants which will provide more control over other polymer attributes such as stereochemistry and cross-linking.

These catalysts are particularly useful to create homopolymers. However, they should also be useful in creating copolymers.

It has also been surprisingly learned that too high levels of elemental potassium in the synthesis reaction (e.g. 3.0 molar equivalent or above) can cause significant ring degradation and purification problems. On the other hand, too low an elemental potassium level in the reaction (e.g. 2.1 molar equivalent or below) can lead to undesirably long required reaction times (e.g. sometimes days are required for the reaction). Thus, a narrow range of molar equivalency is highly preferred.

Advantages of the present invention include providing:
(a) methods of the above kind for catalyzing the production of polymers;
(b) polymers of the above kind which are produced by these methods; and
(c) methods of the above kind for more efficiently synthesizing such catalysts.

These and still other advantages of the present invention will be apparent from the description which follows. The description is merely of the preferred embodiments. The claims should therefore be looked to in order to understand the full scope of the invention.

DETAILED DESCRIPTION OF THE INVENTION

Most of the examples discussed below used the following "Catalyst I" as the catalyst:

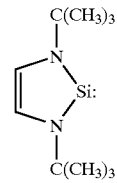

One possible means of synthesizing this catalyst is described in M. Denk et al., 116 J. Am. Chem. Soc. 2691–2692 (1994).

However, we prefer to modify the last step of this synthesis (the reaction of the dihalide) as follows. In our experiment we provide a three-neck 1000 mL flask equipped with a stir bar, reflux condenser and two stoppers was charged with 19.36 g (72.4 mmol) of a precursor (where M=Si, R$^1$ and R$^2$=H, and R$^3$ and R$^4$=t-butyl). 350 mL of THF was added to the dichloride precursor to dissolve the compound and yield an approximately 0.2 M solution. This was stirred vigorously, while 6.51 g of elemental potassium (166.60 mmol, 2.3 molar equivalents) was cut into small chunks.

The potassium was rinsed with hexane to remove mineral oil and then added to the dichloride solution all at once under a heavy flow of argon. Once the potassium had been added, the solution was set to reflux for three hours. The reaction was monitored by $^1$H NMR, and upon complete conversion to the silylene (3 hours), the reaction was stopped, cooled, and filtered through a medium-porosity frit to remove potassium chloride. Upon filtration the solvent was removed in vacuo to yield dark red solid. This solid was sublimed at 90° C. and 30 mtorr to yield 9.95 g (70.0%) of the pale yellow silylene.

EXAMPLE 1

In this experiment we reacted Catalyst I with 2,3-dimethyl-1,3-butadiene to create a butadiene polymer. Into a 50 mL Schlenk flask, 0.20 g of Catalyst I (1.02 mmol) was added. A stir bar was added and the silylene was dissolved in 20 mL of dry THF. The solution was cooled in a dry ice/acetone bath. The butadiene (0.12 mL, 1.0 mmol), pre-distilled away from its radical inhibitor at 30 C. under static vacuum, was injected into the silylene solution and the reaction mixture was allowed to warm to room temperature.

After several hours of stirring in the dark, a yellowish insoluble material became evident. $^1$HNMR of the reaction mixture indicated that only silylene material was present. The precipitate was insoluble in CH$_2$Cl$_2$, benzene, toluene, THF, hexane, acetone, DMSO, acetonitrile and water indicating a high degree of cross-linking.

The IR spectrum of the insoluble material was consistent with the formation of a butadiene polymer. This reaction was repeated with more standard catalytic amounts (5 mol %) of silylene, again resulting in the formation of polymer. IR (KBr pellet) 2600–2900 cm$^{-1}$ (aliphatic C—H stretches).

EXAMPLE 2

In this experiment we reacted Catalyst I with styrene to create polystyrene. Into a 50 mL Schlenk flask, 0.50 g of Catalyst I (2.55 mmol) was added. A stir bar was added and the silylene was dissolved in 20 mL of dry THF. The solution was cooled in a dry ice/acetone bath. Styrene (0.30 mL, 2.6 mmol), predistilled away from its catechol inhibitor at 30 C. under static vacuum, was injected into the silylene solution and the reaction mixture was allowed to warm to room temperature.

After several hours of stirring in the dark, a white insoluble material became evident. $^1$HNMR of the reaction mixture indicated that only silylene material was present. The precipitate was insoluble in $CH_2Cl_2$, benzene, toluene, THF, hexane, acetone, DMSO, acetonitrile and water.

The IR spectrum of the insoluble material was consistent with the formation of a polystyrene polymer. This reaction was repeated with more standard catalytic amounts (5 mol %) of silylene, again resulting in the formation of polymer. IR (KBr pellet) 697 $cm^{-1}$ (s, ring C=C bend), 750 $cm^{-1}$ (s, aromatic C—H bend in plane), 1060 $cm^{-1}$ (s, aromatic C—H bend, out of plane), 1630–1650 $cm^{-1}$ (s,C=C stretches), 1667–2000 $cm^{-1}$ (w, aromatic overtone bands), 2800–2960 $cm^{-1}$ (vs, methylene stretches), 3000–3100 $cm^{-1}$ (s, aromatic C—H stretches)

EXAMPLE 3

Experiments similar to Example 2 were conducted, albeit with varied solvents from THF. To a stirring solution containing 0.230 g (1.17 mmol) of Catalyst I silylene in hexane was added 3.00 mL (26.2 mmol) of styrene at room temperature. After 5 minutes of stirring the solution became cloudy with fine white precipitate. After 30 minutes the solution was full of polystyrene.

After one hour, the solution was filtered and the resulting filtrate was concentrated to dryness to yield the silylene. Confirmation by NMR revealed that about 80% of the silylene was recovered along with about 5% of the water adduct of the silylene. The resulting polymer was recovered to yield 0.35 g of the insoluble material.

We then tried toluene as the solvent. Excess styrene was injected into a solution of Catalyst I in toluene. The reaction did not produce the insoluble material as quickly as in hexane. An aliquot was pulled after 30 minutes revealing the solution contents:
silylene and styrene. The mixture was stirred for a period of 3 hours, whereupon insoluble material appeared. This reaction was stirred overnight to complete the reaction. The solution was filtered after 15 hours of stirring at room temperature to yield 0.11 g of polymer and nearly all the silylene.

Thus, the reaction solvent used, while preferably organic, is not critical.

EXAMPLE 4

In this experiment we reacted Catalyst I with 1-hexene to create polyhexene (poly-1-hexene). To a solution of silylene in hexane was added a 20 fold excess of 1-hexene. After 30 minutes of stirring at room temperature, the solution was cloudy with an insoluble material. After 3.0 hours of stirring, the solution was so full of precipitate it appeared as if there were very little solvent left in the flask.

When the flask was purged with $N_2$ and opened, there was no smell of hexene left coming from the mixture. The mixture was filtered and the filtrate was evaporated to dryness yielding 82% of the silylene recovered. Also, 0.34 g of polymer was produced. This reaction was also performed in toluene, and provided a similar type of result as that for styrene. All the silylene was recovered and all of the polymer was recovered after 24 hours of reaction time.

EXAMPLE 5

In this experiment we reacted Catalyst I with propene to create polypropene (polypropylene). Silylene, 0.23 g (1.22 mmol) was dissolved in 15 mL of hexane in a Schlenk flask. The flask was fitted with a septum and propene was bubbled in at room temperature. No reaction was seen after 30 minutes of bubbling. An aliquot was subsequently pulled out and tested by NMR to see if the silylene was still intact. The NMR experiment revealed only Catalyst I in solution.

The flask was then fitted with a glass stopper and the solution was frozen in liquid nitrogen and all inert gas was removed in vacuo. Propene was then used to backfill the flask to approximately 25 psi. As the mixture was warmed excess propene was released. After achieving room temperature, the mixture was stirred for 5 minutes and became cloudy. After 15 minutes the solution became cloudier with precipitate. After one hour of stirring at room temperature, the reaction mixture was filtered yielding 0.14 g of polymer and 0.17 g of silylene (74%).

EXAMPLE 6

In this experiment we reacted Catalyst I with ethene to create polyethene (polyethylene). A solution containing 0.17 g (0.87 mmol) of Catalyst I in 15 mL of hexane was frozen in liquid $N_2$ and all inert gas was removed. The flask was backfilled with ethene (25 psi) and allowed to warm to room temperature. Once this was achieved, the solution was stirred for 15 minutes and became cloudy. After 4 hours of stirring, there was no change in the mixture. This was set to stir overnight. After 24 hours the solution was filtered to give 20 mg of polymer and 0.15 g of silylene (88%).

EXAMPLE 7

In this experiment we reacted Catalyst I with 2,3-dimethyl butadiene to create polybutadiene. About a 25 fold excess of butadiene was added to a Schlenk flask containing Catalyst I in hexane. After 20 minutes the flask was full of precipitate. This was filtered and nearly all silylene was recovered.

EXAMPLE 8

To a 100 mL Schlenk flask was added 0.11 g (0.56 mmol) of Catalyst I followed by 5 mL of hexane. After Catalyst I was dissolved into solution, 0.74 mL (11.2 mmol) of acrylonitrile was added to the solution. The reaction mixture immediately became cloudy and after one minute all the solid formed coagulated into one lump of yellow solid. The solid was filtered and dried and analyzed using IR spectroscopy, revealing the formation of polyacrylonitrile. Catalyst I was isolated (0.08 g 73%) from the reaction as well as 0.6 g (50%) of the polymer.

EXAMPLE 9

Using the same procedure shown above, to a 100 mL Schlenk containing 0.046 g. (0.23 mmol) of Catalyst I dissolved in 5 mL of hexane, was added 0.5 mL (6.0 mmol) of vinylidene chloride. The reaction was stirred for 2 hours after which solid had formed. This solution was set to stir overnight at room temperature. The solid was filtered off to give 0.116 g (20%) of polymer identified as poly-vinylidene chloride. Catalyst I was recovered (0.041 g, 90%).

EXAMPLE 10

To a 100 mL Schlenk was added 0.25 g. (1.22 mmol) of Catalyst I followed by 20 mL of hexane. To this was added 2.44 mL (25.5 mmol) of ethyl vinyl ether. The solution appeared pale yellow even after 2 hours. The solution was set to stir overnight. After 18 hours, the solution was full of precipitate, which was filtered to yield 0.45 g (25%) of poly-ethyl vinyl ether. Catalyst I was recovered (0.24 g. 95%).

EXAMPLE 11

We have also tried a fully saturated version of Catalyst I (two extra hydrogens instead of the ring double bonded carbon). This catalyst ("Catalyst II") was the compound referred to as Compound "2" in M. Haaf et al., 120 J. Am. Chem. Soc. 12714–12719 (1998). This compound exists as a tetramer in the solid state. We needed to stir a solution for 2 hours to break up the tetramer in order to form the silylene. To a 100 mL Schlenk was added 0.23 g. (1.16 mmol) of saturated silylene Catalyst II and 20 mL of THF. This red solution was stirred for 2 hours and eventually became light yellow. 1-hexene was added (1.43 mL, 11.6 mmol) and the solution remained the same pale yellow. After 4 hours the solution became colorless and contained a white precipitate, which was filtered and identified as poly-1-hexene. Polymer recovered: 0.29 g. 30%.

EXAMPLE 12

We also tried another version of Catalyst I where the double bonded carbon is also part of a phenyl ring ("Catalyst III"). This is the compound referred to as Compound "3" in M. Haaf et al., 120 J. Am. Chem. Soc. 12714–12719 (1998). To a 50 mL Schlenk was added 0.057 g. (0.21 mmol) of the silylene Catalyst III followed by 5 mL of hexane. 1-hexene (0.64 mL, 5.19 mmol) was added all at once to the silylene solution. After 30 minutes, the solution became cloudy and was filtered after 3 hours to yield 0.12 g (28%) of poly-1-hexene. Nearly all of the silylene (0.054 g. 95%) was recovered.

EXAMPLE 13

In this experiment we reacted Catalyst I with phenylacetylene to create poly-phenylacetylene. To a stirring solution containing 0.22 g (1.12 mmol) of Catalyst I and 20 mL of hexane, was added 2.44 mL (22.41 mmol) of phenylacetylene all at once. The solution turned from the original pale yellow to a dark orange solution with precipitate instantaneously. An aliquot was pulled from the reaction mixture and was analyzed by $^1$H NMR to reveal only Catalyst I was present after 15 minutes. The cloudy solution was let stir for one hour and filtered. The resulting polymer (110 mg) was filtered off and the silylene was recovered from the resulting filtrate.

General Discussion

All reactions involving Catalyst I were run under strict Schlenk conditions (emphasizing the absence of water and oxygen). Room temperature proved suitable for the reactions. For solid reaction components, atmospheric pressure was sufficient. For gaseous monomers (e.g. ethene and propene) we preferred to use a pressure of about 25 psi.

The styrene polymer was found to be insoluble in every solvent we tried, even including hot toluene (120° C.). The hexene polymer was also fairly insoluble in many solvents. The propene polymer was not very soluble in toluene until in was heated to 90° C. and some solid dissolved into the solvent.

The present invention thus provides catalysts, particularly for use in polymerization reactions. While particular catalysts have been emphasized in the above experiments, it is expected that a wide variety of silylenes (particularly heterocyclic partially unsaturated compounds) will be effective for catalyzing a wide variety of polymerization reactions.

INDUSTRIAL APPLICABILITY

The present invention provides methods for producing catalysts, and for using them to facilitate production of polymers, and also provides polymers manufactured using these methods.

We claim:

1. A method for producing a polymer comprising polymerizing monomers selected from the group consisting of terminal alkene monomers and terminal alkyne monomers, in the presence of a catalyst selected from the group consisting of cyclic silylenes.

2. The method of claim 1, wherein the catalyst has a [N—Si—N] moiety with these three atoms being part of an at least partially unsaturated heterocyclic ring of at least five and no more than ten atoms.

3. The method of claim 1, wherein the catalyst is:

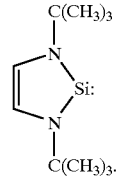

* * * * *